United States Patent
Shirai et al.

(10) Patent No.: US 7,643,141 B2
(45) Date of Patent: Jan. 5, 2010

(54) METHOD AND APPARATUS FOR INSPECTING COLOR FILTER

(75) Inventors: Toru Shirai, Mie (JP); Yasuhiro Kohara, Mie (JP); Morihide Ohsaki, Mie (JP); Kenji Takii, Mie (JP)

(73) Assignee: Sharp Kabushiki Kaisha, Osaka-Shi (JP)

( * ) Notice: Subject to any disclaimer, the term of this patent is extended or adjusted under 35 U.S.C. 154(b) by 508 days.

(21) Appl. No.: 11/658,671

(22) PCT Filed: Jul. 22, 2005

(86) PCT No.: PCT/JP2005/013910

§ 371 (c)(1),
(2), (4) Date: Jan. 29, 2007

(87) PCT Pub. No.: WO2006/011506

PCT Pub. Date: Feb. 2, 2006

(65) Prior Publication Data
US 2009/0190134 A1 Jul. 30, 2009

(30) Foreign Application Priority Data
Jul. 30, 2004 (JP) .............................. 2004-224111

(51) Int. Cl.
G01N 21/00 (2006.01)
G01N 21/25 (2006.01)
(52) U.S. Cl. .................... 356/239.2; 356/416; 356/419
(58) Field of Classification Search ... 356/237.1–241.6, 356/426–431, 600–640
See application file for complete search history.

(56) References Cited

U.S. PATENT DOCUMENTS

| | | | | |
|---|---|---|---|---|
| 4,422,752 A | * | 12/1983 | Thurm et al. | 355/41 |
| 5,032,007 A | * | 7/1991 | Silverstein et al. | 349/79 |
| 5,355,234 A | * | 10/1994 | Kim | 358/512 |
| 5,400,135 A | * | 3/1995 | Maeda | 356/239.1 |
| 5,773,173 A | * | 6/1998 | Nakano et al. | 430/30 |
| 6,221,544 B1 | * | 4/2001 | Hayashi et al. | 430/7 |
| 6,842,240 B2 | * | 1/2005 | Ueta | 356/239.2 |

FOREIGN PATENT DOCUMENTS

| | | | |
|---|---|---|---|
| JP | 56129844 A | * | 10/1981 |
| JP | 61-38537 A | | 2/1986 |
| JP | 4-37711 A | | 2/1992 |
| JP | 5-99787 A | | 4/1993 |
| JP | 11-101691 A | | 4/1999 |
| JP | 2004-325963 A | | 11/2004 |

* cited by examiner

*Primary Examiner*—Gregory J Toatley, Jr.
*Assistant Examiner*—Jarreas C Underwood
(74) *Attorney, Agent, or Firm*—Birch, Stewart, Kolasch & Birch, LLP

(57) ABSTRACT

A method for inspecting a color filter includes a first step of disposing the color filter so that the color filter is opposed to a light source, a second step of outputting, from the light source, monochromatic light of a color corresponding to one of the colors of color layers of the color filter and entering the light into the plurality of color layers, and a third step of inspecting for display unevenness in each of the color layers with light transmitted through the color layers.

24 Claims, 5 Drawing Sheets

METHOD AND APPARATUS FOR INSPECTING COLOR FILTER

TECHNICAL FIELD

The present invention relates to method and apparatus for inspecting a color filter, and more particularly relates to inspection for display unevenness in a color layer of a color filter.

BACKGROUND ART

In recent years, demands for thin display devices such as a color liquid crystal display device have been dramatically increased. With the increased demands, higher display quality has been strongly desired. Such a display device includes a color filter in which color layers of three primary colors, i.e., red (R), green (G) and blue (B) are arranged in a predetermined pattern. Therefore, in order to improve display quality, it is essential to fabricate the color filters with high accuracy.

As methods for fabricating the color filter, in general, a staining method, an inkjet method, a printing method, a photolithography method and the like have been known. Among such known color filter fabrication methods, photolithography is currently a mainstream because the number of process steps is relatively small and high controllability and resolution can be achieved.

In photolithography, a color resist is applied to a substrate to form a color layer, and then the color layer is exposed to light through a photomask. Thereafter, the exposed color resist is developed to form a color layer each having a predetermined pattern. Thus, a color filter is fabricated.

If a foreign material is mixed in the color filter, the foreign material itself intercepts display light or the foreign material protrudes into a display medium such as a liquid crystal layer to give an adverse effect to display quality. Therefore, the color filter fabrication process steps are performed in a very clean environment with special attention to prevent mixture of a foreign material into the color layer. However, mixture of a foreign material into the color layer can not be completely prevented.

Moreover, there might be cases where part of the color layer is peeled during fabrication process steps and defective part is created. In such a case, light transmitted through the defective part is not colored and output from a light source as it is. Thus, the light transmitted through the defective part is observed as light leakage.

To cope with this problem, then, it is conventionally known that the inspection step of inspecting for the existence of mixture of a foreign material and defective part is performed to a manufactured color filter. For example, as shown in FIG. 5, a method in which white light is entered in a color filter and an inspector observes transmitted light for inspection is known.

Specifically, in the inspection method, a color filter 103 is disposed so as to be located between an inspector 101 and a light source 102 for outputting white light. In the color filter 103, color layers 103r of R, color layers 103g of G and color layers 103b of B are formed. The color layers 103r transmits only red light in a predetermined wavelength range of incident white light therethrough and output the red light to the inspector side. In the same manner, the color layers 103g transmits only green light through and the color layers 103b transmits only blue light therethrough. If the existence of mixture of a foreign material, defective part or the like is found in any one of the color layers 103r, 103g and 103b, the existence of the foreign material, defective part or the like is observed as abnormal output light by the inspector 101.

However, in the above-described inspection method, light outgoes simultaneously from each of a plurality of color layers 103r, 103g and 103b, and therefore, for example, even if defective part is created in one of the color layers 103r of R and outgoing light from the color layer 103r is changed, it is difficult to accurately and speedily distinguish the change in the outgoing light from the specific color layer. Accordingly, an enormous time is required for reliable inspection, thus resulting in increase in production cost.

As shown in FIG. 6, it is known to dispose an inspection filter 105 between the color filter 103 and the inspector 101 in the above-described inspection method (see, for example, Patent Reference 1). The inspection filter 105 is formed so as to transmit light in a predetermined wavelength range therethrough and largely cuts light transmitted through normal part of the red, green, and blue color layers. On the other hand, light transmitted through the defective part has the whole wavelength range of visible light and the ratio of light being cut by the inspection filter 105 can be reduced. Thus, the contrast between light transmitted through the normal part and light transmitted through the defective part 106 is increased, so that inspection for the defective part 106 can be performed in a simple manner.

(Patent Reference 1) Japanese Laid-Open Publication No. 5-99787

DISCLOSURE OF INVENTION

Problems that the Invention is to Solve

For photolithography, besides a method in which a liquid color resist is applied to a substrate to provide a color resist on the substrate, a method in which a color resist film is attached to a substrate (dry film lamination, also referred to as "DFL"). By DFL, unlike a method in which a color resist is applied, the process step of baking is not necessary and the number of process steps can be advantageously reduced.

However, using DFL, there might be cases where display unevenness is caused in a color layer by waviness of a resist film itself, a tension added to a resist film in attaching the resist film and the like. The display unevenness occurs due to slight change in the thickness of a color layer or change in the aperture ratio of a color layer.

Moreover, display unevenness in a color layer occurs when the color layer is formed not only by the above-described DFL but also by a method in which a liquid color resist is applied. As display unevenness which commonly occurs in the above-described two methods, there are display unevenness due to a development defect in the step of development, display unevenness due to deformation of etched part of a pattern of a color layer and display unevenness due to non-uniformity of a pattern pitch and a pattern width of a color layer.

To improve display quality, it is absolutely necessary to reliably detect faulty display due to the above-described display unevenness. However, display faulty due to the above-described display unevenness is minor one, compared to faulty display due to mixture of a foreign material and a defect, and it is difficult to detect such display unevenness.

To cope with this, an inspection filter can be disposed between an inspector and a color filter as in Patent Reference 1. However, unlike defective part, with display unevenness, incident white light does not pass therethrough as it is, and therefore the contrast between part of the color layer in which the display unevenness has occurred and normal part thereof can not be increased. That is, it is difficult to reliably detect display unevenness.

In the view of the above-described points, the present invention has been devised and it is therefore an object of the present invention to reliably and simply detect display unevenness in a color layer of a color filter and improve display quality.

Means for Solving the Problems

To achieve the above-described object, according to the present invention, monochromatic light is entered into a color layer of a color filter to detect the existence of display unevenness in a color layer.

Specifically, a method for inspecting a color filter according to the present invention is a method for inspecting a color filter including a plurality of color layers provided for each of a plurality of colors on a transparent substrate, and includes: a first step of disposing the color filter so that the color filter is opposed to a light source; a second step of outputting, from the light source, monochromatic light of a color corresponding to one of the plurality of colors of the plurality of color layers in the color filter and entering the monochromatic light into the plurality of color layers; and a third step of inspecting for the existence of display unevenness in the color layers with light transmitted through the color layers.

It is preferable that the monochromatic light to be entered into the plurality of color layers is changed in order so that a color of the monochromatic light corresponds to each of the colors of the color layers.

Moreover, a method for inspecting a color filter according to the present invention is a method for inspecting a color filter including a plurality of color layers provided for each of a plurality of colors on a transparent substrate. The method includes: a first step of disposing the color filter so that the color filter is opposed to a light source including a generator section for generating white light and a monochromatic filter for transmitting only monochromatic light among the white light generated in the generator section through the monochromatic filter; a second step of outputting, from the monochromatic filter of the light source, monochromatic light of a color corresponding to one of the plurality of colors of the color layers in the color filter and entering the monochromatic light to the plurality of color layers; and a third step of inspecting for the existence of display unevenness in the color layers with light transmitted through the color layers.

It is preferable that the monochromatic light to be entered into the plurality of color layers is changed in order by changing the monochromatic filter of the light source so that a color of the monochromatic light corresponds to each of the colors of the color layers.

It is preferable that the ratio of part of light output from the light source and transmitted through inspection target ones of the color layers which is interfered by light output from the light source and transmitted through other ones of the color layers to the light transmitted through the inspection target ones is 0% or more and less than 30%.

A wavelength range of the light transmitted through the inspection target ones of the color layers may be 590 nm or more and 780 nm or less. Also, a wavelength range of the light transmitted through the inspection target ones of the color layers may be 515 nm or more and 585 nm or less.

It is preferable that the monochromatic light output from the light source is light in a wavelength range which makes a transmittance of inspection target ones of the color layers is 10% or more.

A wavelength range of the light transmitted through the inspection target ones of the color layers may be 580 nm or more and 685 nm or less. Also, a wavelength range of the light transmitted through the inspection target ones of the color layers may be 475 nm or more and 605 nm or less. Moreover, a wavelength range of the light transmitted through the inspection target ones of the color layers may be 385 nm or more and 535 nm or less.

Moreover, an apparatus for inspecting a color filter includes: a supporting section for supporting a color filter including a plurality of color layers provided for each of a plurality of colors on a transparent substrate; and a light source for outputting monochromatic light for each of the plurality of colors so that a color of the monochromatic light corresponds to each color of the plurality of color layers, and is so configured that the monochromatic light output from the light source is entered into the color layers to inspect for the existence of display unevenness in the color layers.

Effects

According to a method for inspecting a color filter according to the present invention, when the existence of display unevenness is inspected for, first in the first step, a color filter is disposed so as to be opposed to a light source. Subsequently, in the second step, monochromatic light is output from the light source and the monochromatic light is entered into a plurality of color layers of the color filter. The color layers are disposed on a transparent substrate for each color (such as red, green, and blue). Then, the color of the monochromatic light output from the light source corresponds to one of the colors of the color layer.

Thereafter, in the third step, the incident monochromatic light into the plurality of color layers is transmitted through ones of the color layers of a color corresponding to the color of the monochromatic light. As a result, ones of the color layers of a color corresponding to the color of the monochromatic light are inspected for the existence of display unevenness with the transmitted light. In this case, the transmitted light through the color filter is monochromatic, so that display unevenness in a color layer, which is less prone to be detected than mixture of a foreign material and a defect, can be reliably detected in a simple manner.

By changing the color of the monochromatic light to different one of the colors of the color layers in order, inspection of all of the color layers of the color filter can be performed for each of the colors of the color layers.

Moreover, when the light source includes a generator for generating white light and a monochromatic filter, in the second step, only monochromatic light in a predetermined wavelength range among white light generated in the generator section is transmitted through the monochromatic film and is output as a whole from the light source. The monochromatic light output from the light source is transmitted through color layers of one of the plurality of colors, and thus the existence of display unevenness in the color layers through which the monochromatic light has been transmitted are inspected.

As for light output from the light source and transmitted through inspection target ones of the color layers, if the ratio of part of the light which is interfered by light output from the light source and transmitted through other ones of the color layers is 30% or more of the light transmitted through the inspection target ones, the interfered part becomes too large, so that it becomes difficult to visually identify the transmitted light. Therefore, by making the ratio of the interfered part be 0% or more and less than 30%, the transmitted light through the inspection target ones of the color layers can be visually identified in a simple manner. Thus, the existence of display unevenness can be reliably detected.

Specifically, when light transmitted through the inspection target ones of the color layers is red light in a wavelength range of 590 nm or more and 780 nm or less, or green light in a wavelength range of 515 nm or more and 585 nm or less, the ratio of the interfered part can be made to be 0% or more and less than 30%.

Moreover, if the transmittance of the monochromatic light output from the light source to the inspection target ones of the color layers is less than 10%, it becomes difficult to visually identify the light transmitted through the inspection target ones of the color layers at a sufficient level. Therefore, by determining the wavelength range of monochromatic light output from the light source so that the transmittance of the inspection target ones of the color layers becomes 10% or more, it is possible to perform reliable inspection.

Specifically, when light transmitted through the inspection target ones of the color layers is red light in a wavelength range of 580 nm or more and 685 nm or less, green light in a wavelength range of 475 nm or more and 605 nm or less, or blue light in a wavelength range of 385 nm or more and 535 nm or less, the ratio of the interfered part can be made to be 10% or less.

Moreover, with an apparatus for inspecting a color filter according to the present invention, when the existence of display unevenness is inspected for, a color filter is placed onto a supporting section so that the supporting section supports the color filter. Then, monochromatic light output from the light source for each color is entered into the color layers of the color filter. Thus, the color layers are inspected for the existence of display unevenness therein for each color of the color layers.

Furthermore, when the light source includes a generator section for generating white light and a monochromatic filter, only monochromatic light in a predetermined wavelength range among white light generated in the generator section is transmitted through the monochromatic filter and is output as a whole from the light source. The monochromatic light output from the light source is transmitted through ones of the color layers of one of the plurality of colors, and thus the existence of display unevenness in the color layers of the color through which the monochromatic light has been transmitted can be inspected.

Effect of the Invention

According to the present invention, by entering monochromatic light into color layers of a color filter, light of a different color from the color of inspection target color layers can be suppressed and light used for inspection can be made monochromatic. Thus, display unevenness in a color layer, which is less prone to be detected than mixture of a foreign material and a defect, can be reliably detected in a simple manner, and display quality can be improved.

BEST MODE FOR CARRYING OUT THE INVENTION

Hereinafter, embodiments of the present invention will be described with reference to the accompanying drawings. Note that the present invention is not limited to the following embodiments.

Embodiment 1

Figure 1:
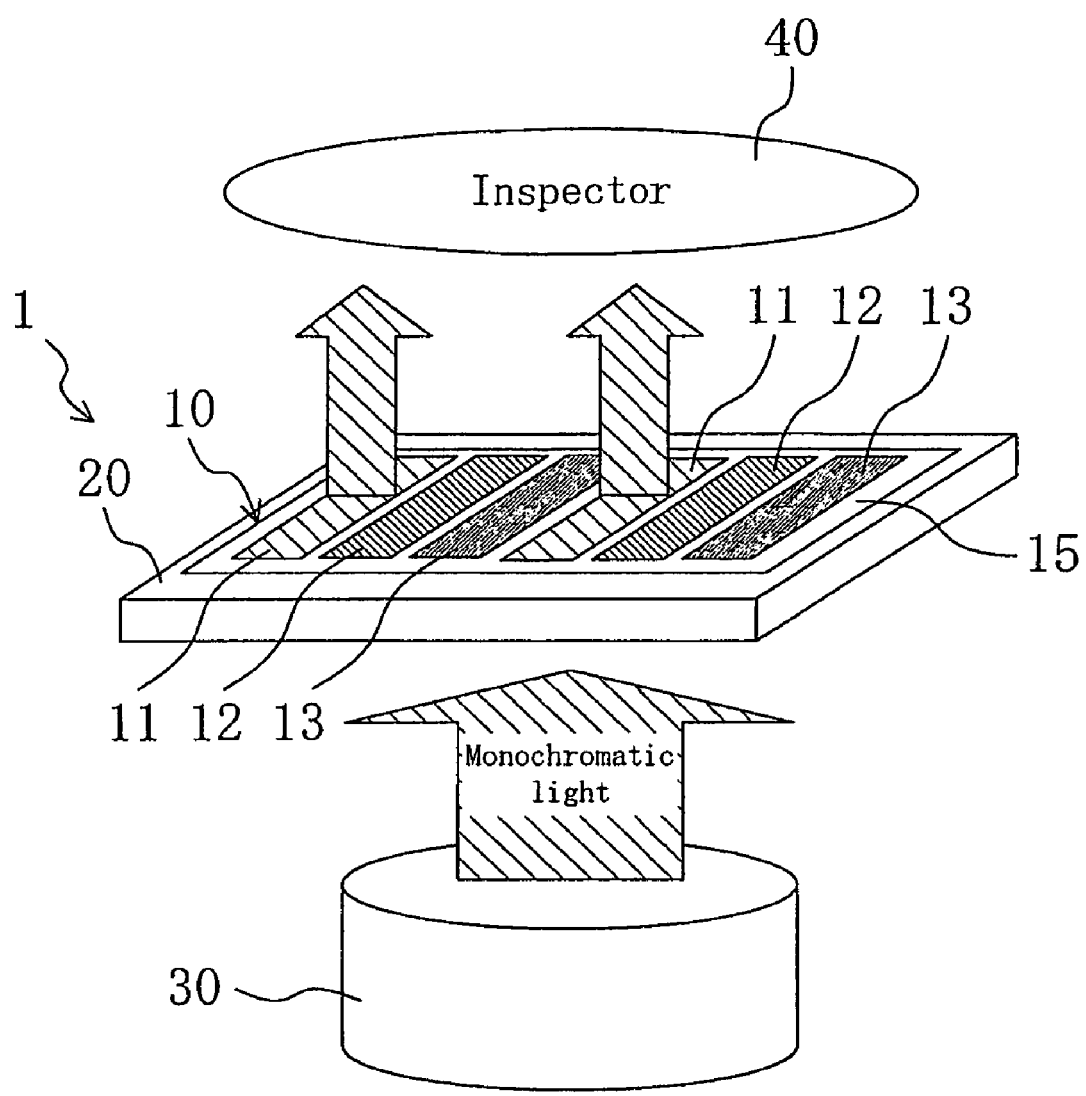
FIG. 1 is a perspective view schematically illustrating inspection method and apparatus according to Embodiment 1 of the present invention.
Figure 2:
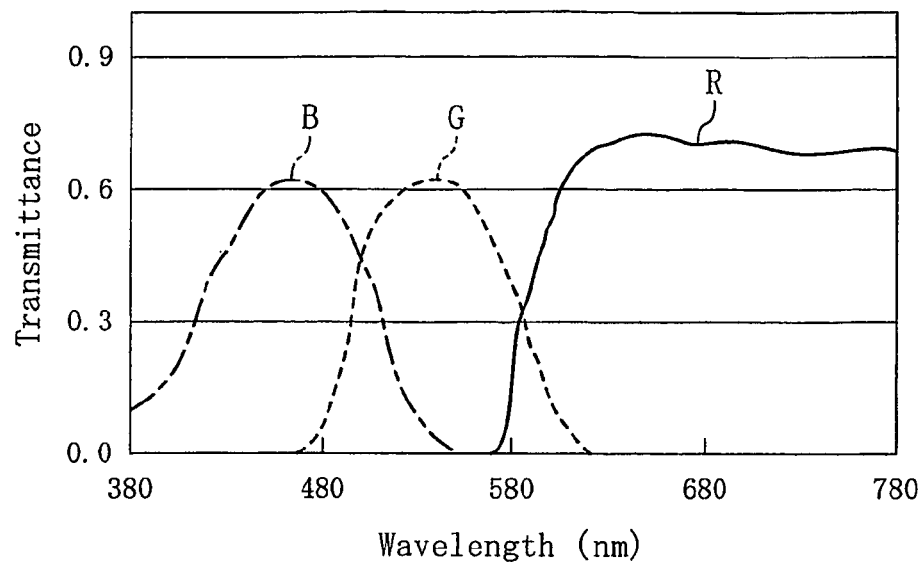
FIG. 2 is a graph showing spectral transmittance characteristics for color layers of note colors.
Figure 3:
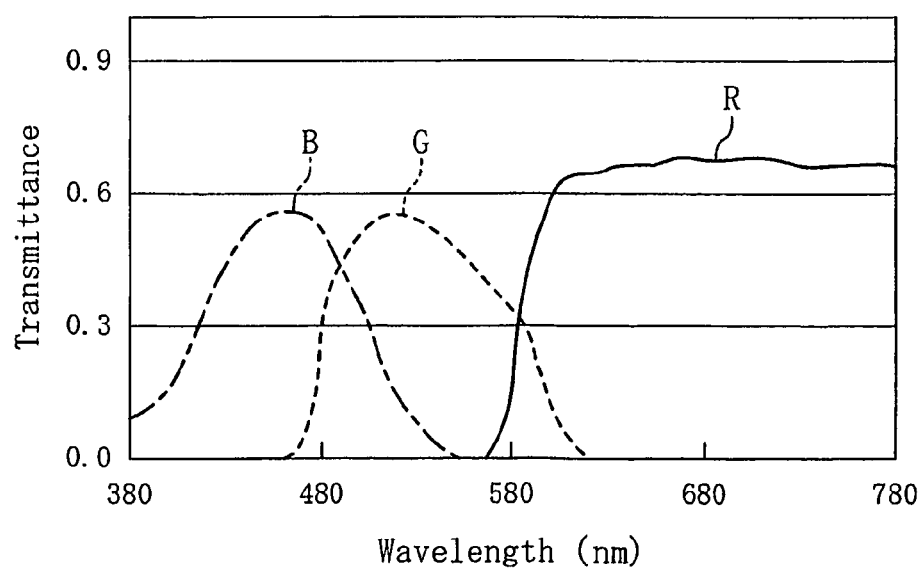
FIG. 3 is a graph showing spectral transmittance characteristics for color layers of monitor colors.

FIGS. 1, 2 and 3 are for describing method and apparatus for inspecting a color filter according to Embodiment 1 of the present invention. FIG. 1 is a perspective view schematically illustrating the inspection apparatus of Embodiment 1.

As shown in FIG. 1, the inspection apparatus 1 includes a supporting section 20 for supporting a color filter 10 and a light source 30 for entering light into the color filter 10 for inspection.

The color filter 10 is applied to, for example, a liquid crystal display device. Specifically, although not shown in the drawings, a liquid crystal display device includes a TFT substrate on which a plurality of thin film transistors (TFTs) are disposed and a counter substrate disposed so as to be opposed to the TFT substrate with a liquid crystal layer interposed therebetween. The color filter 10 is provided on the counter substrate. The liquid crystal layer is driven by a TFT on the TFT substrate to perform color display with incident light transmitted through the color filter 10.

The color filter 10 includes a plurality of color layers 11, 12 and 13 provided on a transparent substrate 15 such as a glass substrate for each of a plurality of colors. Specifically, the color layers 11 are for displaying the color of red (R), the color layers 12 are for displaying the color of green (G), and the color layers 13 are for displaying the color of blue (B) and the color layers 11, 12 and 13 are regularly arranged in order. Each of the color layers 11, 12 and 13 is formed of a color resist on the transparent substrate 15 by patterning using photolithography.

The color layers 11, 12 and 13 are formed by DFL (dry film lamination). Specifically, for example, a color resist which is red and has a film form is attached to the transparent substrate 15 with uniform tension applied thereto. Subsequently, exposure is performed to the transparent substrate 15 through a photomask (not shown) to leave a predetermined pattern thereon and then the pattern is developed, thereby forming a plurality of color layers 11. Thereafter, for the color layers 12 of green and the color layers 13 of blue, patterning is performed thereto in the same manner, so that the color filter 10 in which the color layers 11, 12 and 13 of three colors are formed by patterning is obtained.

The color layers 11, 12 and 13 of this embodiment exhibit spectral transmittance characteristics shown in FIGS. 2 and 3. Moreover, in FIGS. 1 and 2, a solid line indicates the transmittance of the red (R) color layers 11, a broken line indicates the transmittance of the green (G) color layers 12 and an alternate long and short dash line indicates the transmittance of the blue (B) color layers 13.

FIG. 2 is a graph showing characteristics of color layers (which will be hereinafter referred to as "note colors") used in a display panel such as a notebook computer. The note color has characteristics that allow reduction in power consumption while maintaining display quality. On the other hand, FIG. 3 is a graph showing characteristics of color layers (which will be hereinafter referred to as "monitor colors") used for a display panel for desktop computer and the like. The monitor color has characteristics with focus on reproducibility for reproducing display color, compared to the note color.

The supporting section 20 is formed of a plate member having an opening (not shown) in a center portion thereof. The color filter 10 is placed onto the supporting section 20, so that the color layers 11, 12 and 13 of the color filter 10 correspond to the opening of the supporting section 20 and a peripheral portion (frame region) of the color filter 10 is entirely attached with a supporting surface of part of the supporting section 20 located around the opening.

The light source 30 is so configured to output monochromatic light of a color corresponding to each of the respective colors of the color layers 11, 12 or 13 and enter the monochromatic light into the color layers 11, 12 and 13 of the color filter 10. Specifically, the light source 30 includes light emitting diodes (LEDs) serving as monochromatic light sources, i.e., a plurality of red LEDs, a plurality of green LEDs and a plurality of blue LEDs. Among the LEDs, only the red LEDs are turned ON, thereby outputting red monochromatic light. In the same manner, only the green LEDs are turned ON, thereby outputting green monochromatic light and only the blue LEDs are turned ON, thereby outputting blue monochromatic light. The color of incident monochromatic light into the plurality of color layers 11, 12 and 13 is changed so as to correspond to the color of each of the color layers 11, 12 and 13 in order. In this embodiment, the light source 30 includes the LEDs of three colors, and thus the color of monochromatic light output from the light source 30 can be changed in a simple manner.

An inspector 40 visually identifies transmitted light of the color filter 10 for each color from an opposing side to the light source 30 through the color filter 10 to inspect for the existence of display unevenness in each of the color layers 11, 12 and 13.

In this case, for example, it is preferable that for light emitting characteristics of the red LEDs, a light emitting peak is 638 nm and a half-value breadth is 18 nm. For light emitting characteristics of the green LEDs, a light emitting peak is preferably 560 nm and a half-value breadth is preferably 15 nm. Furthermore, for light emitting characteristics of the blue LEDs, a light emitting peak is preferably 385 nm or more to 465 nm or less.

However, for a current general-purpose-use light source, a light emitting peak is preferably 468 nm and a half-value breadth is preferably 26 nm.

Moreover, as for light output from the light source 30 and transmitted through ones of the color layers 11, 12 and 13 which are to be inspected, the ratio of part of the light which is interfered by light output from the light source 30 and transmitted through other ones of the color layers 11, 12, and 13 than the inspection targets is preferably 0% or more and less than 30% of the entire light transmitted through the inspection targets. If the interfered part of the light is 30% or more of the entire light transmitted through the inspection targets, the part of light transmitted through the inspection targets which is interfered by the light transmitted through other ones of the color layers 11, 12, and 13 than the inspection targets becomes too large, so that it becomes difficult to visually identify display unevenness.

Specifically, as shown in Table 1, the wavelength range of light output to the color layers 11, 12 and 13, which exhibits the characteristics shown in FIGS. 2 and 3 (note color and monitor color), and transmitted through the red (R) color layers 11 as inspection targets is preferably 590 nm or more and 780 nm or less. Moreover, the wavelength range of light transmitted through the green (G) color layers 12 as inspection targets is preferably 515 nm or more and 585 nm or less. Furthermore, the wavelength range of light transmitted through the blue (B) color layers 13 as inspection targets is preferably 380 nm or more and 480 nm or less. Thus, the ratio of part of light transmitted through inspection target color layers which is interfered by light transmitted through ones of the color layers to be not inspected can be kept at 0% or more and less than 30%.

TABLE 1

| Transmittance of other colors | R (nm) | G (nm) | B (nm) |
|---|---|---|---|
| Less than 5% | 640-670 | 555-570 | 445-465 |
| Less than 10% | 620-635 | 545-575 | 385-465 |
| Less than 30% | 590-780 | 515-585 | 380-480 |

Furthermore, as shown in Table 1, the ratio of the interfered part is preferably 0% or more and less than 10% of the entire light. Specifically, among incident light into the color layers 11, 12 and 13, which exhibits the characteristic shown in FIGS. 2 and 3, the wavelength range of light transmitted through the red (R) color layers 11 as inspection targets is preferably 620 nm or more and 635 nm or less. Moreover, the wavelength range of light transmitted through the green (G) color layers 12 as inspection targets is preferably 545 nm or more and 575 nm or less. Furthermore, the wavelength range of light transmitted through the blue (B) color layers 13 as inspection targets is preferably 385 nm or more and 465 nm or less.

Furthermore, as shown in Table 1, the ratio of the interfered part is preferably 0% or more and less than 5%. Specifically, among incident light into the color layers 11, 12 and 13, which exhibits the characteristic shown in FIGS. 2 and 3, the wavelength range of light transmitted through the red (R) color layers 11 as inspection targets is preferably 640 nm or more and 670 nm or less. Moreover, the wavelength range of light transmitted through the green (G) color layers 12 as inspection targets is preferably 555 nm or more and 570 nm or less. Furthermore, the wavelength range of light transmitted through the blue (B) color layers 13 as inspection targets is preferably 445 nm or more and 465 nm or less. Thus, the ratio of part of light transmitted through inspection targets which is interfered by light transmitted through other ones of the color layers than inspection targets of the color layers can be kept at 0% or more and less than 5%.

Moreover, monochromatic light output from the light source 30 is preferably light in a wavelength range that makes the transmittance of inspection target ones of the color layers 11, 12 and 13 be 10% or more. If the transmittance of monochromatic light output from the light source 30 through inspection target ones of the color layers 11, 12 and 13 is less than 10%, it becomes difficult to visually identify light transmitted through the inspection target ones of the color layers 11, 12 and 13 at a sufficient level.

Specifically, as shown in Table 2, among light output to the color layers 11, 12 and 13, which exhibits the characteristics shown in FIGS. 2 and 3 (note colors and monitor colors), the wavelength range of light transmitted through the red (R) color layers 11 as inspection targets is preferably 580 nm or more and 685 nm or less. Moreover, the wavelength range of light transmitted through the green (G) color layers 12 as inspection targets is preferably 475 nm or more and 605 nm or less. Furthermore, the wavelength range of light transmitted through the blue (B) color layers 13 as inspection targets is preferably 385 nm or more and 535 nm or less. Thus, the ratio of part of light transmitted through inspection targets which is interfered by light transmitted through other ones of the color layers than inspection targets of the color layers can be kept 10% or more.

TABLE 2

| Transmittance | R (nm) | G (nm) | B (nm) |
|---|---|---|---|
| 10% or more | 580-685 | 475-605 | 385-535 |

Inspection Method

Next, a method for inspecting a color filter according to the present invention will be described.

An inspection method according to this embodiment includes a first step, a second step, and a third step. First, in the first step, as shown in FIG. 1, the color filter 10 is placed onto the supporting section 20 so that the color filter 10 is opposed to the light source 30. At this time, the color filter 10 is disposed so that the color layers 11, 12 and 13 correspond to the opening of the supporting section 20.

Thereafter, in the second step, monochromatic light of a color corresponding to one of the colors (R, G and B) of the color layers 11, 12 and 13 is output from the light source 30 and entered into the plurality of the color layers 11, 12 and 13. For example, first, only the red LEDs of the light source 30 are turned ON, thereby outputting red (R) monochromatic light from the light source 30. The red monochromatic light output from the light source 30 enters into each of the color layers 11, 12 and 13 of respective colors and outgoes from the red (R) color layers 11.

Subsequently, in the third step, the inspector 40 inspects for the existence of display unevenness in the color layers 11 with light transmitted through the color layers 11. That is, when display unevenness has occurred in any one of the color layers 11, the display unevenness is visually identified as light and dark irregularity of red transmitted light.

Now, display unevenness which occurs in the color layers 11, 12 and 13 will be described.

Display unevenness in this embodiment is neither defective part in which center part of a color layer is missing nor a foreign material mixed in a color layer. That is, display unevenness is change in an aperture ratio due to very small change in the thickness of a color resist or variation of the area of a pattern of a color resist.

Such display unevenness due to change in the thickness of a color resist is caused by waviness of a resist film itself, non-uniformity of a tension applied to a resist film in attaching the resist film, films being doubly provided by mistake or the like. Moreover, the display unevenness due to change in an aperture ratio is caused by development failure, deformation of an edge portion in a pattern of a color layer, non-uniform pattern pitch or pattern width of a color layer.

After the red color layers 11 have been inspected, the second step is performed again so that for example, only the green LEDs of the light source are turned ON and monochromatic light of green (G) is output. Subsequently, the third step is performed so that the inspector 40 visually identifies transmitted light through the color layers 12 of green (G) to inspect for the existence of display unevenness. Thereafter, the blue (B) color layers 13 are inspected in the same manner as the inspection for the red color layers 11 and the green color layers 12. In the above-described manner, inspection of the color layers 11, 12 and 13 is performed for each color.

Effects of Embodiment 1

According to Embodiment 1, by entering monochromatic light into the color layers 11, 12 and 13 of the color filter 10, transmitted light of other colors than the color of light transmitted through inspection target color layers can be eliminated, so that inspection with light of a single color can be performed. Thus, display unevenness in the color layers 11, 12 and 13, which is less prone to be detected than mixture of a foreign material and a defect, can be reliably detected in a simple manner. As a result, display quality can be improved.

Moreover, part of light output from the light source 30 and transmitted through inspection target ones of the color layers 11, 12 and 13 which is interfered by light output from the light source 30 and transmitted through other ones of the color layers 11, 12, and 13 than the inspection targets is made to be 0% or more and less than 30% of the light transmitted through the inspection target color layers. Thus, light transmitted through the inspection target ones of the color layers 11, 12 and 13 can be visually identified with high accuracy. Therefore, inspection can be performed very precisely.

Moreover, monochromatic light in a wavelength range that makes a transmittance of each of the color layers 11, 12 and 13 be 10% or more is output from the light source 30. Thus, light of a desired color can be visually identified with a high brightness. Therefore, inspection accuracy can be increased.

Embodiment 2

Figure 4:
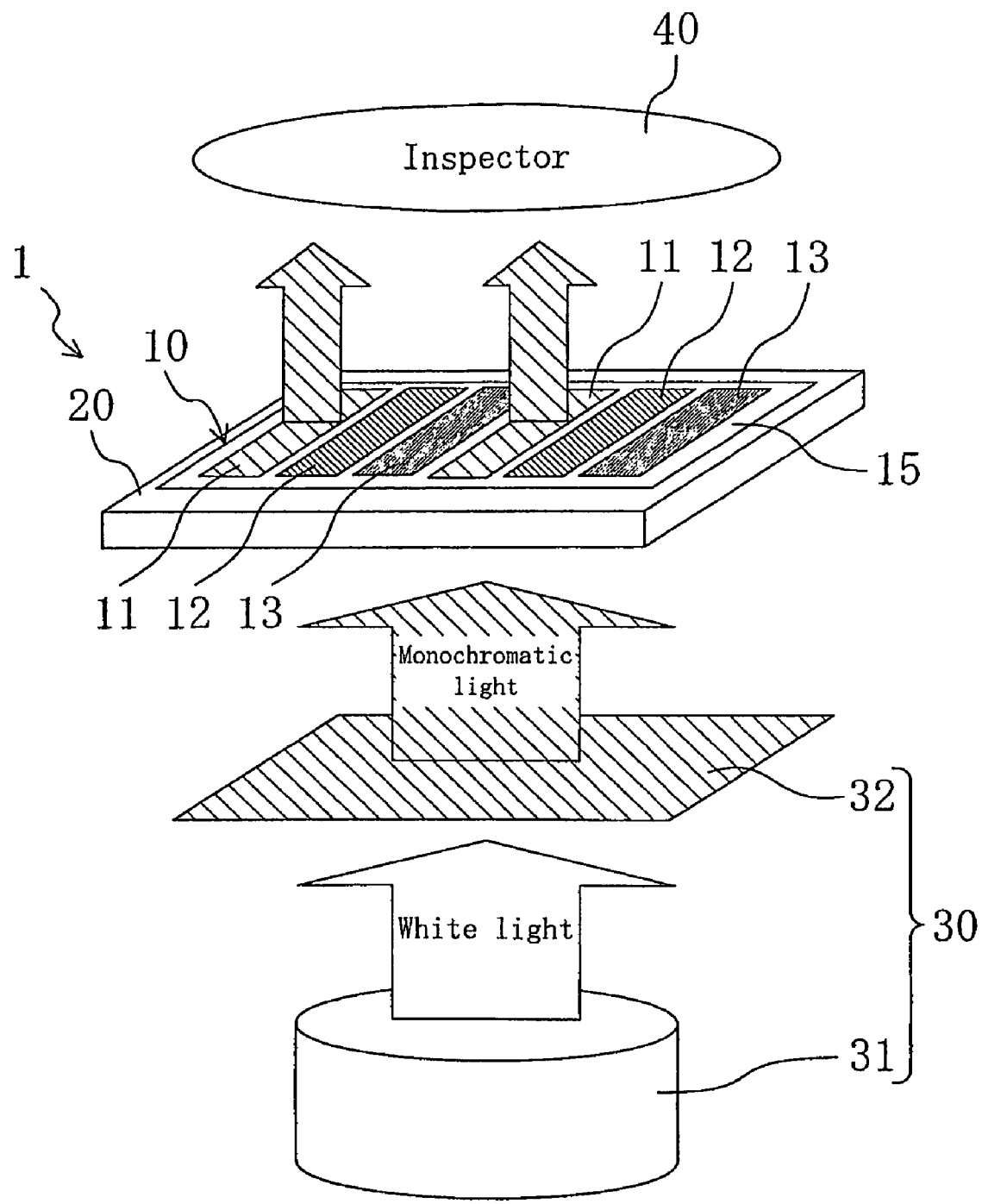
FIG. 4 is a perspective view schematic illustrating inspection method and apparatus according to Embodiment 2 of the present invention.
Figure 5:
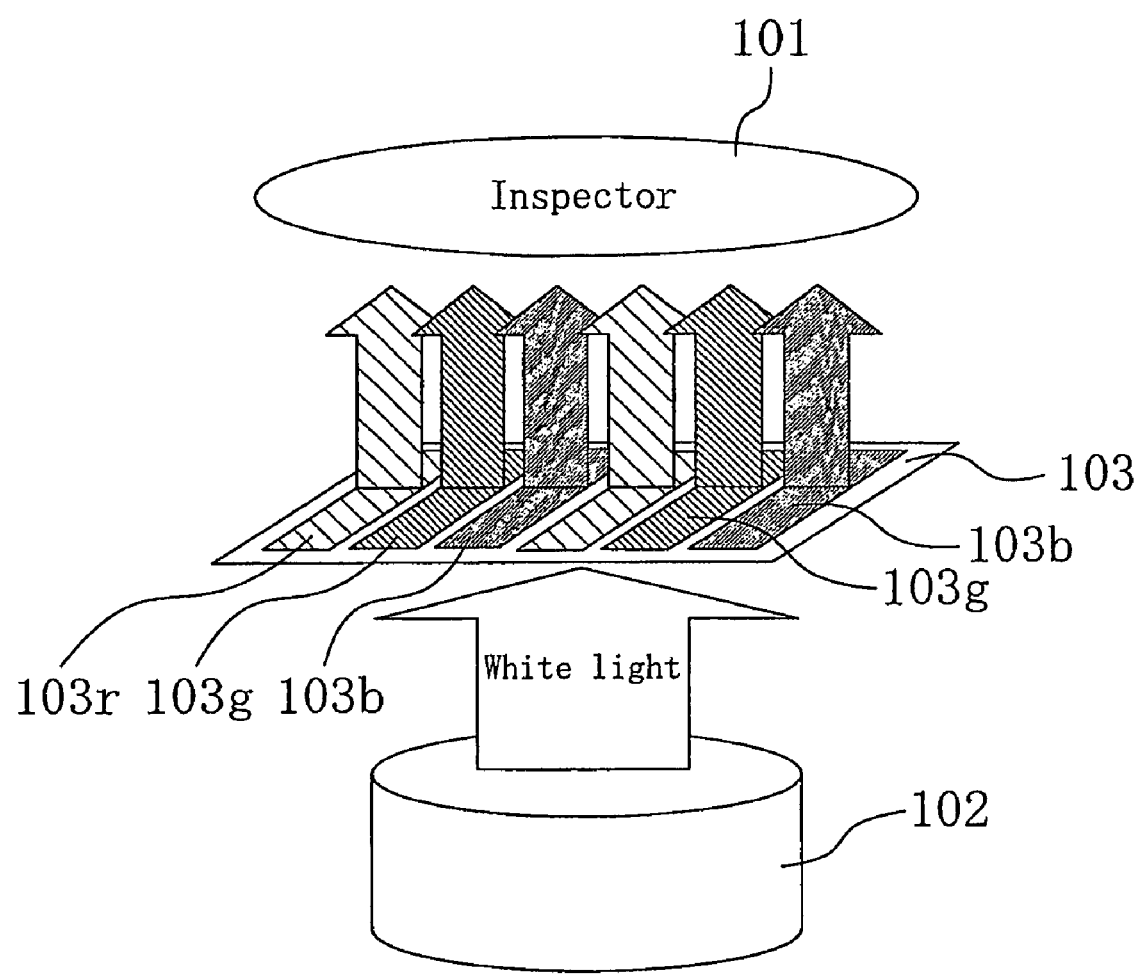
FIG. 5 is a perspective view schematically illustrating a known inspection method for detecting foreign material mixed part or defective part.
Figure 6:
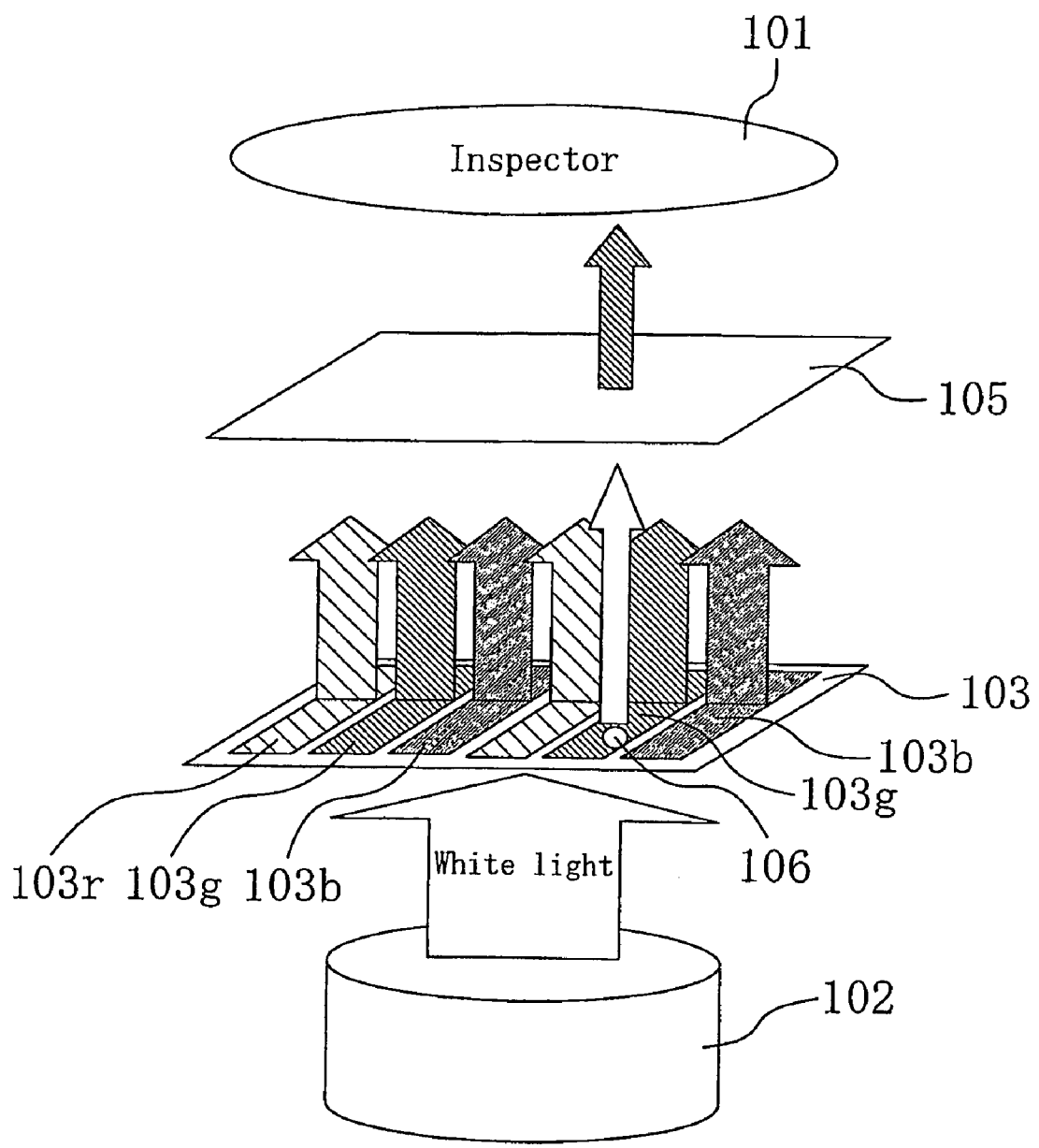
FIG. 6 is a perspective view schematically illustrating a known inspection method for detecting defective part.

FIG. 4 is a perspective view describing method and apparatus for inspecting a color filter according to Embodiment 2 of the present invention. In each of the following embodiments, each member also described in Embodiment 1 is identified by the same reference numeral and therefore the description thereof will be omitted.

In this embodiment, as shown in FIG. 4, the light source 30 includes a generator section 31 for generating white light and monochromatic filters 32 for transmitting only monochromatic light in a predetermined wavelength range among lights generated by the generator section 31. The light source 30 as a whole outputs monochromatic light.

The generator section 31 is formed of, for example, a fluorescence lamp or the like. On the other hand, as for the monochromatic filters 32, red (R), green (G) and blue (B) monochromatic filters are formed of TS-R-62 or TS-R-64 (manufactured by TOKIWA OPTICAL CORPORATION), TS-G-545 (manufactured by TOKIWA OPTICAL CORPORATION) and TS-B-390 or TS-B-440 (manufactured by TOKIWA OPTICAL CORPORATION), respectively. The light source 30 includes the monochromatic filters 32 of three colors corresponding to respective colors of color layers 11, 12 and 13. With exchange of the monochromatic filters 32, a film color is changed, thereby outputting monochromatic light of red (R), green (G) or blue (B) each time.

Thus, as in Embodiment 1, the first step, the second step and the third step are performed for inspection for the existence of display unevenness in the color layers 11.

Effects of Embodiment 2

According to Embodiment 2, the same effects as those of Embodiment 1 can be also achieved. Moreover, the filters 32 are provided in an inspection apparatus and thus the inspector does not have to repeatedly replace a filter. Therefore, inspection cane be performed in a simple manner.

Other Embodiments

In Embodiment 1, as the light source 30, a plurality of LEDs of three colors, i.e., R, G and B are provided. However, the present invention is not limited thereto. For example, instead of LEDs, an improved triple wavelength tube for use in a fluorescence lamp and the like can be used. Specifically, although not shown in the drawings, the triple wavelength tube includes a pair of ignition electrodes, a gas for generating ultraviolet light in response to discharge generated between ignition electrodes, and a luminous body for emitting light when ultraviolet light is irradiated thereto. A regular triple wavelength tube outputs white light, but if characteristics of the luminous body are changed such that the luminous body emits only light in a predetermined wave length range, a light emitting lamp for outputting monochromatic light of one of colors of R, G and B can be formed. Thus, by providing a plurality of light emitting lamps of the colors R, G and B, instead of LEDs provided for each color in Embodiment 1, a light source for outputting monochromatic light of a single color for each of R, G or B can be obtained.

INDUSTRIAL APPLICABILITY

As has been described, the present invention is useful for method and apparatus for inspecting a color filter for the existence of display unevenness in color layers of the color filter. Specifically, the present invention is suitable to the case where display unevenness is reliably detected in a simple manner to improve display quality.

The invention claimed is:

1. A method for inspecting a color filter including a plurality of color layers provided for each of a plurality of colors on a transparent substrate, the method comprising:
   a first step of disposing the color filter so that the color filter is opposed to a light source;
   a second step of outputting, from the light source, monochromatic light of a color corresponding to one of the plurality of colors of the plurality of color layers in the color filter and entering the monochromatic light into the plurality of color layers; and
   a third step of inspecting for the existence of display unevenness in the color layers with light transmitted through the color layers.

2. The method of claim 1, wherein the monochromatic light to be entered into the plurality of color layers is changed in order so that a color of the monochromatic light corresponds to each of the colors of the color layers.

3. The method of claim 1, the ratio of part of light output from the light source and transmitted through inspection target ones of the color layers which is interfered by light output from the light source and transmitted through other ones of the color layers to the light transmitted through the inspection target ones is 0% or more and less than 30%.

4. The method of claim 3, wherein a wavelength range of the light transmitted through the inspection target ones of the color layers is 590 nm or more and 780 nm or less.

5. The method of claim 3, wherein a wavelength range of the light transmitted through the inspection target ones of the color layers is 515 nm or more and 585 nm or less.

6. The method of claim 1, wherein the monochromatic light output from the light source is light in a wavelength range which makes a transmittance of inspection target ones of the color layers be 10% or more.

7. The method of claim 6, wherein a wavelength range of the light transmitted through the inspection target ones of the color layers is 580 nm or more and 685 nm or less.

8. The method of claim 6, wherein a wavelength range of the light transmitted through the inspection target ones of the color layers is 475 nm or more and 605 nm or less.

9. The method of claim 6, wherein a wavelength range of the light transmitted through the inspection target ones of the color layers is 385 nm or more and 535 nm or less.

10. A method for inspecting a color filter including a plurality of color layers provided for each of a plurality of colors on a transparent substrate, the method comprising:
    a first step of disposing the color filter so that the color filter is opposed to a light source including a generator section for generating white light and a monochromatic filter for transmitting only monochromatic light among the white light generated in the generator section through the monochromatic filter;
    a second step of outputting, from the monochromatic filter of the light source, monochromatic light of a color corresponding to one of the plurality of colors of the color layers in the color filter and entering the monochromatic light to the plurality of color layers; and
    a third step of inspecting for the existence of display unevenness in the color layers with light transmitted through the color layers.

11. The method of claim 10, wherein the monochromatic light to be entered into the plurality of color layers is changed in order by changing the monochromatic filter of the light source so that a color of the monochromatic light corresponds to each of the colors of the color layers.

12. The method of claim 10, wherein the ratio of part of light output from the light source and transmitted through inspection target ones of the color layers which is interfered by light output from the light source and transmitted through other ones of the color layers to the light transmitted through the inspection target ones is 0% or more and less than 30%.

13. The method of claim 12, wherein a wavelength range of the light transmitted through the inspection target ones of the color layers is 590 nm or more and 780 nm or less.

14. The method of claim 12, wherein a wavelength range of the light transmitted through the inspection target ones of the color layers is 515 nm or more and 585 nm or less.

15. The method of claim 10, wherein the monochromatic light output from the light source is light in a wavelength range which makes a transmittance of inspection target ones of the color layers be 10% or more.

16. The method of claim 15, wherein a wavelength range of the light transmitted through the inspection target ones of the color layers is 580 nm or more and 685 nm or less.

17. The method of claim 15, wherein a wavelength range of the light transmitted through the inspection target ones of the color layers is 475 nm or more and 605 nm or less.

18. The method of claim 15, wherein a wavelength range of the light transmitted through the inspection target ones of the color layers is 385 nm or more and 535 nm or less.

19. An apparatus for inspecting a color filter, the apparatus comprising:
    a supporting section for supporting a color filter including a plurality of color layers provided for each of a plurality of colors on a transparent substrate; and
    a light source for outputting monochromatic light for each of the plurality of colors so that a color of the monochromatic light corresponds to one of the plurality of color layers, wherein the monochromatic light output from the light source is entered through the color layers to inspect for the existence of display unevenness in the color layers.

20. The apparatus of claim 19, the ratio of part of light output from the light source and transmitted through inspection target ones of the color layers which is interfered by light output from the light source and transmitted through other ones of the color layers to the light transmitted through the inspection target ones is 0% or more and less than 10%.

21. The apparatus of claim 19, the monochromatic light output from the light source is light in a wavelength range which makes a transmittance of inspection target ones of the color layers be 10% or more.

22. An apparatus for inspecting a color filter, the apparatus comprising:
   a supporting section for supporting a color filter including a plurality of color layers provided for each of a plurality of colors on a transparent substrate; and
   a light source including a generator section for generating white light and a monochromatic filter for transmitting only monochromatic light,
   wherein the apparatus is so configured that light output from the light source is entered through the color layers to inspect display unevenness in the color layers.

23. The apparatus of claim 22, the ratio of part of light output from the light source and transmitted through inspection target ones of the color layers which is interfered by light output from the light source and transmitted through other ones of the color layers to the light transmitted through the inspection target ones is 0% or more and less than 10%.

24. The apparatus of claim 22, the monochromatic light output from the light source is light in a wavelength range which makes a transmittance of inspection target ones of the color layers be 10% or more.

* * * * *